United States Patent
Walters

(10) Patent No.: US 6,878,157 B1
(45) Date of Patent: Apr. 12, 2005

(54) TRIGGER TO ACTIVATE SUPERCOOLED AQUEOUS SALT SOLUTION FOR USE IN A HEAT PACK

(75) Inventor: Matthew Walters, 17810 Keystone Trail Ct., Chesterfield, MO (US) 63005

(73) Assignee: Matthew Walters, St. Louis, MO (US)

( * ) Notice: Subject to any disclaimer, the term of this patent is extended or adjusted under 35 U.S.C. 154(b) by 0 days.

(21) Appl. No.: 09/989,591

(22) Filed: Nov. 20, 2001

Related U.S. Application Data

(60) Provisional application No. 60/276,295, filed on Mar. 16, 2001.

(51) Int. Cl.$^7$ .................................................. A61F 7/03
(52) U.S. Cl. .................................. 607/108; 126/263.03
(58) Field of Search .................. 126/263; 607/104–114

(56) References Cited

U.S. PATENT DOCUMENTS

| | | | |
|---|---|---|---|
| 1,433,010 A | 10/1922 | Hogan | |
| 1,915,523 A | 6/1933 | Ferguson | |
| 2,220,777 A | 11/1940 | Othmer | |
| 2,289,425 A | 7/1942 | Hogan | |
| 3,093,308 A | 6/1963 | Snelling | |
| 4,077,390 A | 3/1978 | Stanley et al. | |
| 4,572,158 A | 2/1986 | Fiedler | |
| 4,872,442 A * | 10/1989 | Manker | 126/263.04 |
| 5,275,156 A | 1/1994 | Milligan et al. | |
| 5,305,733 A | 4/1994 | Walters | |
| 5,736,110 A * | 4/1998 | Angelillo et al. | 422/245.1 |
| 5,915,461 A * | 6/1999 | Tanhehco | 165/46 |
| 6,283,116 B1 * | 9/2001 | Yang | 126/263.03 |
| 6,318,359 B1 * | 11/2001 | Schmidt et al. | 126/263.03 |
| 6,537,309 B2 * | 3/2003 | Sharma et al. | 126/263.03 |

* cited by examiner

*Primary Examiner*—Roy D Gibson
*Assistant Examiner*—Henry M Johnson, III
(74) *Attorney, Agent, or Firm*—Linda L. Lewis; Peter S. Gilster; Greensfelder, Hemker & Gale, P.C.

(57) ABSTRACT

A trigger to activate a supercooled aqueous salt solution wherein the solution is encased in a flexible container to form a heat pack, the trigger made of dry or partially dry particles adhering to a support so that when the trigger is manipulated, allowing the dry or partially dry particles to be released and contact the supercooled salt solution, crystallization is initiated and heat is released.

18 Claims, 4 Drawing Sheets

TRIGGER TO ACTIVATE SUPERCOOLED AQUEOUS SALT SOLUTION FOR USE IN A HEAT PACK

CROSS-REFERENCE TO RELATED APPLICATION

This application claims the priority of Provisional Patent Application Ser. No. 60/276,295, entitled "TRIGGER TO ACTIVATE SUPERCOOLED AQUEOUS SALT SOLUTION FOR USE IN A HEAT PACK" filed Mar. 16, 2001, continued preservation of which is requested.

FIELD OF THE INVENTION

This invention relates to a trigger to activate a supercooled aqueous salt solution wherein the solution is encased in a flexible container to form a heat pack. The trigger is made of dry or partially dry particles adhering to a support. When the trigger is manipulated, allowing the dry or partially dry particles to be released and contact the supercooled salt solution, crystallization is initiated and heat is released.

BACKGROUND OF THE INVENTION

Heat packs utilizing supercooled aqueous salt solution have been used for the treatment of soreness of muscles of athletes and sportsmen. Heat packs are also used as infant heel warmers in medical facilities as an aid in drawing blood. Such supercooled solutions include aqueous solutions of sodium acetate and calcium nitrate tetrahydrate.

Various techniques of initiating crystallization have been proposed, including inserting a crystal of material into the supercooled solution, injecting air by means of a valve, scraping metal into the container, and squeezing a plurality of rigid objects. Examples of these techniques and others are disclosed in U.S. Pat. Nos. 1,915,523, 1,433,010, 2,289,425, 2,220,777, 3,093,308, 4,077,390, 4,572,158, 5,275,156 and 5,305,733.

The present invention provides a trigger made from a support material to which adhere dry or partially dry particles. Such a trigger is typically made from sand paper which is easily manufactured and used. The trigger is used by manipulating to cause the dry or partially dry particles to be released into the salt solution. Preferably, the trigger can be activated using one hand. None of the above references disclose the claimed invention.

SUMMARY OF THE INVENTION

The present invention relates to a trigger to initiate crystallization of a supercooled aqueous salt solution wherein the trigger is made of dry or partially dry particles adhering to a support. A preferred trigger is made from sandpaper. When the trigger is immersed in the salt solution and manipulated to release dry or partially dry particles, crystallization is initiated and heat is released. The present invention further relates to a heat pack comprising a supercooled aqueous salt solution and a trigger encased in a flexible container, wherein the trigger is made from a support material to which adhere dry or partially dry particles. When the trigger is manipulated, dry or partially dry particles are released, thereby initiating crystallization. Optionally, the trigger is sandpaper is in the form of a disc and is coated with a water-resistant resin

BRIEF DESCRIPTION OF THE DRAWINGS

The above advantages may be more clearly understood from the following detailed description and by reference to the drawings.

DETAILED DESCRIPTION OF THE PREFERRED EMBODIMENT

Figure 1:
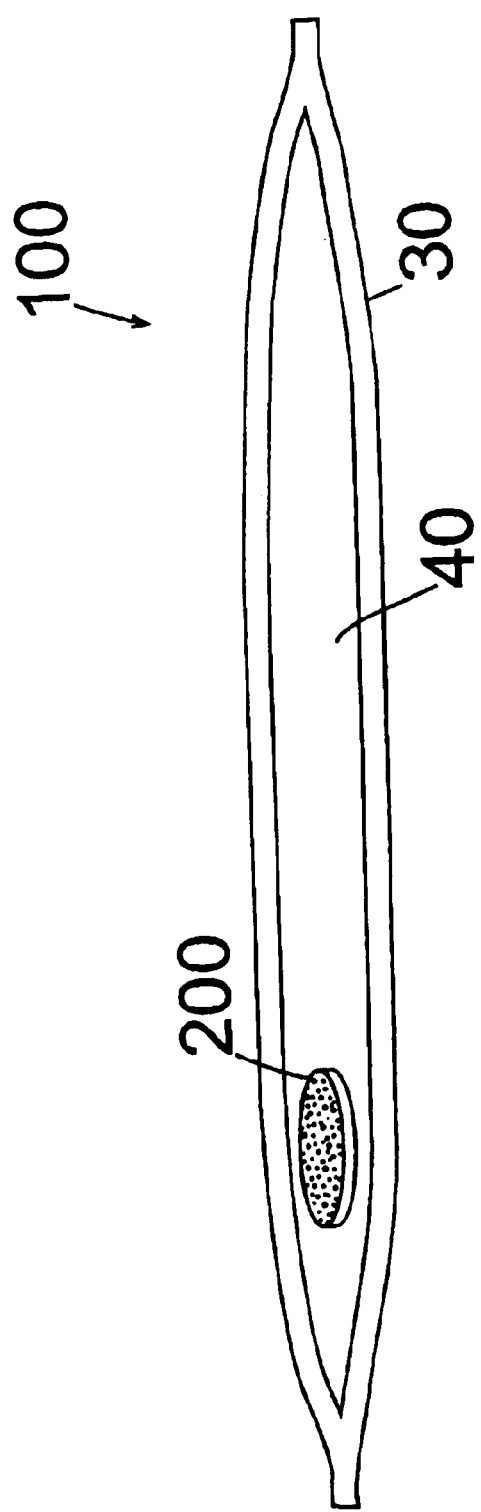
FIG. 1 is a side, sectional view of the heat pack and trigger, wherein the trigger is not activated.
Figure 2A:
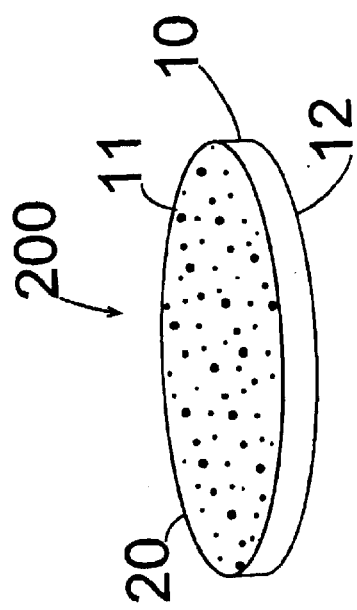
FIG. 2A is a side view of the trigger, not activated, with an optional coating.
Figure 2B:
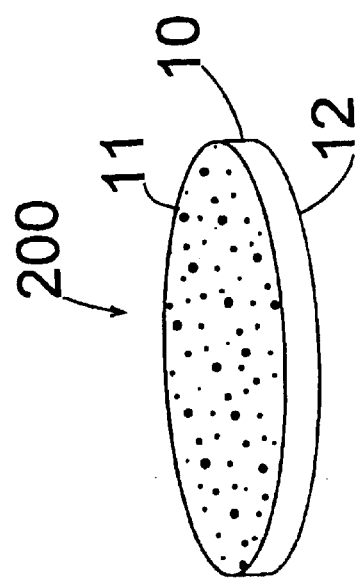
FIG. 2B is a side view of the trigger, not activated, uncoated.
Figure 3:
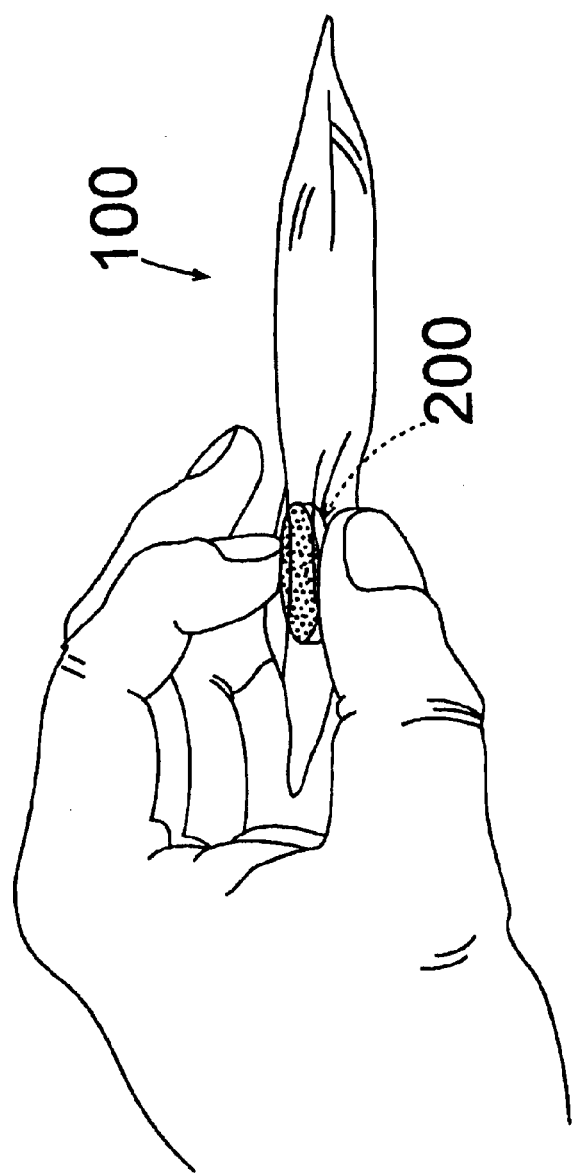
FIG. 3 is a side view of the heat pack with the trigger being manipulated to activate.

Referring to FIGS. 1, 2 and 3, a heat pack 100 having a trigger 200 made of a support material to which dry or partially dry particles adhere 10, optionally coated with a water resistant resin 20 has a flexible container 30 which contains a supercooled salt solution 40 which, when activated, releases heat. Suitable solutions include supercooled sodium acetate, lead acetate, calcium nitrate tetrahydrate, sodium pyrophosphate and sodium thiosulfate solutions. The preferred solution is sodium acetate, which is generally harmless to humans.

The salt solution 40 is made by dissolving the salt in the desired amount of water. The amount of salt to be utilized should permit the salt solution to be supercooled to at least the ambient temperature at which the heat pack is intended to be utilized. Said solutions are disclosed in U.S. Pat. No. 5,305,733, which is hereby incorporated by reference.

Flexible container 30 of heat pack 100 can be made from any water-tight flexible material not adversely affected by the supercooled solution. Preferably, the flexible material is able to withstand the temperatures (generally on the order of about 60° to 65° C.) to which the heat pack 100 can be heated to re-dissolve the precipitated salt in order to reuse the pack. Suitable flexible materials include plastics such as rubber, vinyl, vinyl-coated fabric, nylon polylaminate and polyethylene. Preferably, the flexible container is made from nylon polylaminate of a thickness in the range of about 1 mil (0.026 mm) to 10 mils (0.26 mm).

A trigger 200 is made of support material to which adheres dry or partially dry particles 10 optionally coated with a water resistant coating 20, as shown in FIG. 2A. The support material can have particles on one side or both. Preferably, the trigger is made from sandpaper 10 which has a rough side 11 and a smooth side 12. The roughness of the sandpaper can be the result of sand, or other abrasive materials such as aluminum oxide, adhering to the paper. A preferred trigger is emery cloth, which has aluminum oxide particles cemented to a fabric. When the rough side of the sandpaper trigger is manipulated by flexing, rubbing or kneading, aggregate particles break off, causing a dry or partially dry side of the aggregate to contact the supercooled solution. The dry or partially dry particles activate the heatpack, causing crystallization and subsequent heat release.

The optional water resistant coating 20 need only be applied to the rough side 11 of the trigger, although both sides may be coated. The coating should be applied sufficiently thick that the rough side of the sandpaper is covered and remains dry, even when immersed in the supercooled salt solution 40. A suitable coating is a solvent-free adhesive made of 4,4-diphenylmethane diisocyanate sold under the tradename Supergrip 2000. The size and shape of the trigger is not critical. Typically, the trigger is a disc with a diameter in the range of about 1 to 5 cm.

Referring to FIG. 3, the trigger is activated by being manipulated by flexing, rubbing or pinching between the thumb and forefinger. The trigger can be activated with one or two hands. When the trigger is manipulated, dry or partially dry particles are released, activating the heat pack. Optionally, the heat pack can be reused by heating the heat pack and reforming the supercooled solution. For re-use, the trigger 200 is flexed again to release additional dry or partially dry particles to retrigger the heat pack.

Figure 4:
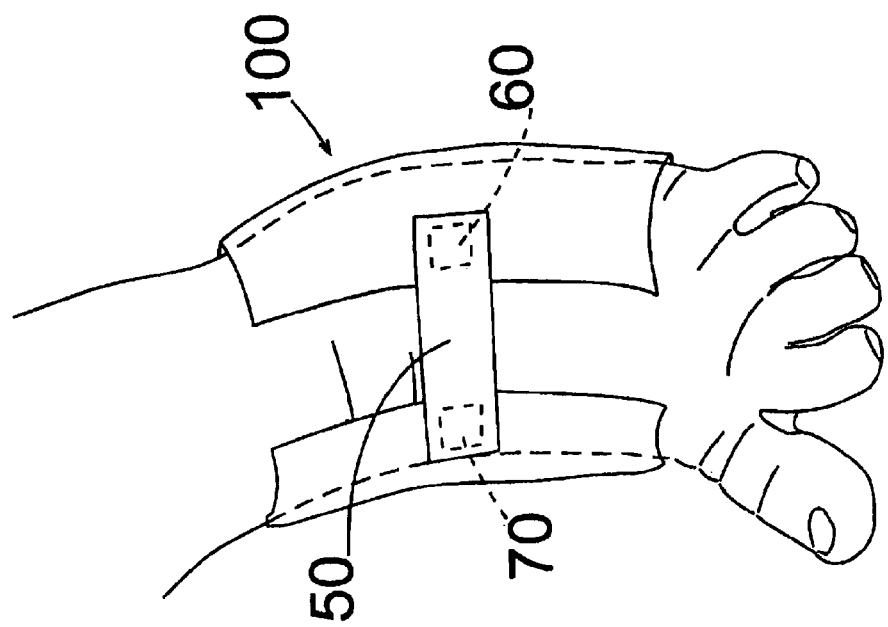
FIG. 4 is a side view of the heat pack fastened to an ankle.

The heat pack of the present invention can be used to heat body parts, such as wrists, ankles, arms and infant heels. In a preferred embodiment, the heat pack has a fastening means for securing the heat pack to a body part. The fastening means can be an elastic band, a contact adhesive applied to the bottom surface of the flexible container, or a strip which encircles the body part. The preferred fastening means is a flexible plastic strip which secures the heat pack to the body part. As shown in FIG. 4, a heat pack 100 is applied to the heel and secured with flexible strap 50. Under either or both ends (60 and 70) of the strap is an adhesive, such as contact adhesive or pressure sensitive adhesive, which allows the strap to be applied and removed.

The invention and its attendant advantages are understood from the foregoing description and it is apparent that various changes may be made in the form, construction and arrangement of the parts without departing from the spirit and scope thereof or sacrificing its material advantages. The arrangements described are merely examples. The claims of the invention are not restricted to the specific forms shown.

What is claimed is:

1. A heat pack comprising a supercooled aqueous salt solution and a trigger encased in a flexible container, wherein the trigger is sandpaper, wherein the salt solution is a sodium acetate solution, wherein the flexible container is made of a nylon polylaminate, wherein the heat pack has a flexible plastic strap as a fastening means, and wherein when the trigger is flexed, dry or partially dry particles are released, thereby initiating crystallization.

2. A trigger to initiate crystallization of a supercooled aqueous salt solution wherein the trigger comprises sandpaper having dry or partially dry particles adhering to a support, wherein, when the dry or partially dry particles are released into the salt solution by manipulation of the support, crystallization is initiated.

3. The trigger of claim 2, wherein the sandpaper has one rough side and one smooth side.

4. The trigger of claim 2, wherein the sandpaper is made of emery cloth with aluminum oxide particles cemented to a fabric.

5. The trigger of claim 2, wherein the trigger is a disc with a diameter of from about 1 to about 5 cm.

6. The trigger of claim 2, wherein the trigger is enclosed in a flexible container of a supercooled salt solution.

7. The trigger of claim 6, wherein the supercooled salt solution is a sodium acetate solution.

8. The trigger of claim 2, wherein the sandpaper is coated.

9. The trigger of claim 2, wherein the sandpaper is coated with a solvent-free adhesive.

10. A heat pack comprising a supercooled aqueous salt solution and a trigger encased in a flexible container, wherein the trigger comprises sandpaper having dry or partially dry particles adhering to a support, wherein, when the dry or partially dry particles are released into the salt solution by manipulation of the support, crystallization is initiated.

11. The heat pack of claim 10, wherein the sandpaper is made of emery cloth with aluminum oxide particles cemented to a fabric.

12. The heat pack of claim 10, wherein the trigger is a disc with a diameter of from about 1 to about 5 cm.

13. The heat pack of claim 10, wherein the supercooled salt solution is selected from the group consisting of supercooled sodium acetate, lead acetate, calcium nitrate tetrahydrate, sodium pyrophosphate and sodium thiosulfate solutions.

14. The heat pack of claim 10, wherein the supercooled salt solution is a sodium acetate solution.

15. The heat pack of claim 10, wherein the flexible container is made from plastics selected from the group consisting of rubber, vinyl, vinyl-coated fabric, nylon polylaminate and polyethylene.

16. The heat pack of claim 10, wherein the flexible container is made from nylon polylaminate.

17. The heat pack of claim 10, wherein the trigger is coated with a water-resistant coating.

18. The heat pack of claim 10, wherein the pack has a fastening means suitable for fastening to a body part.

* * * * *